(12) United States Patent
Smith

(10) Patent No.: US 11,024,304 B1
(45) Date of Patent: Jun. 1, 2021

(54) VIRTUAL ASSISTANT COMPANION DEVICES AND USES THEREOF

(71) Applicant: Revon Systems, Inc., Crestwood, KY (US)

(72) Inventor: Theodore Russell Smith, St. Matthews, KY (US)

(73) Assignee: Zyus Life Sciences US Ltd., Saskatoon (CA)

( * ) Notice: Subject to any disclaimer, the term of this patent is extended or adjusted under 35 U.S.C. 154(b) by 69 days.

(21) Appl. No.: 15/881,132

(22) Filed: Jan. 26, 2018

Related U.S. Application Data

(60) Provisional application No. 62/451,082, filed on Jan. 27, 2017.

(51) Int. Cl.
*G10L 15/22* (2006.01)
*G10L 13/00* (2006.01)
*G06F 3/16* (2006.01)

(52) U.S. Cl.
CPC .............. *G10L 15/22* (2013.01); *G06F 3/167* (2013.01); *G10L 13/00* (2013.01); *G10L 2015/223* (2013.01)

(58) Field of Classification Search
CPC ................................ G10L 13/00; G10L 15/22
See application file for complete search history.

(56) References Cited

U.S. PATENT DOCUMENTS

| | | | | |
|---|---|---|---|---|
| 4,215,240 | A  * | 7/1980 | Ostrowski | G09B 21/00 340/4.14 |
| 5,802,467 | A  * | 9/1998 | Salazar | H04B 10/1149 455/420 |
| 7,174,294 | B2 * | 2/2007 | Schmid | G10L 15/26 704/201 |
| 9,635,164 | B2 * | 4/2017 | Smith | H04M 1/7255 |
| 10,016,162 | B1 * | 7/2018 | Rogers | A61B 5/0022 |
| 10,091,545 | B1 * | 10/2018 | Cwik | H04N 21/439 |
| 2002/0077819 | A1 * | 6/2002 | Girardo | G10L 25/69 704/260 |
| 2003/0036685 | A1 * | 2/2003 | Goodman | G16H 40/63 600/300 |

(Continued)

FOREIGN PATENT DOCUMENTS

| | | | |
|---|---|---|---|
| WO | WO-2004051626 A1 * | 6/2004 | ............. G10L 13/04 |
| WO | WO 2015/191562 A1 | 12/2015 | |
| WO | WO 2016/077792 A1 | 5/2016 | |

OTHER PUBLICATIONS

Hawley, Marks., et al. "A voice-input voice-output communication aid for people with severe speech impairment." IEEE Transactions on neural systems and rehabilitation engineering 21.1 (2012): 23-31. (Year: 2012).*

*Primary Examiner* — Brian L Albertalli

(74) *Attorney, Agent, or Firm* — Frost Brown Todd LLC

(57) ABSTRACT

In some aspects, disclosed herein is a device that stores one or more pre-recorded or dynamically generated voice commands that are capable of activating a virtual assistant via a voice-based user interface and causing the virtual assistant to perform a specific task. The device may be activated manually, e.g., by pushing a button. In some aspects, the device relieves a user of a virtual assistant of the need to speak a specific command in order to cause a virtual assistant to perform a specific task.

24 Claims, 1 Drawing Sheet

(56) References Cited

U.S. PATENT DOCUMENTS

| | | | |
|---|---|---|---|
| 2005/0010416 A1* | 1/2005 | Anderson | G06F 40/20 704/271 |
| 2008/0147406 A1* | 6/2008 | Da Palma | G10L 15/22 704/260 |
| 2009/0306983 A1* | 12/2009 | Bhandari | G06Q 50/24 704/251 |
| 2011/0301954 A1* | 12/2011 | Sims | G10L 15/20 704/246 |
| 2011/0313774 A1* | 12/2011 | Ji | G06F 19/3418 704/275 |
| 2012/0016678 A1 | 1/2012 | Gruber et al. | |
| 2013/0183944 A1* | 7/2013 | Mozer | H04L 12/282 455/414.1 |
| 2014/0074454 A1* | 3/2014 | Brown | G10L 15/08 704/9 |
| 2014/0370841 A1 | 12/2014 | Roberts et al. | |
| 2015/0186156 A1 | 7/2015 | Brown et al. | |
| 2015/0243163 A1* | 8/2015 | Shoemake | H03M 13/09 367/197 |
| 2015/0248881 A1* | 9/2015 | Holdren | G10L 15/06 704/260 |
| 2016/0093304 A1 | 3/2016 | Kim et al. | |
| 2017/0039324 A1 | 2/2017 | Francois et al. | |
| 2017/0103757 A1* | 4/2017 | Yamamoto | G10L 15/22 |
| 2017/0269975 A1* | 9/2017 | Wood | G06F 3/167 |
| 2018/0096684 A1* | 4/2018 | Goote | G10L 15/22 |
| 2018/0182393 A1* | 6/2018 | Shim | G10L 15/22 |

* cited by examiner

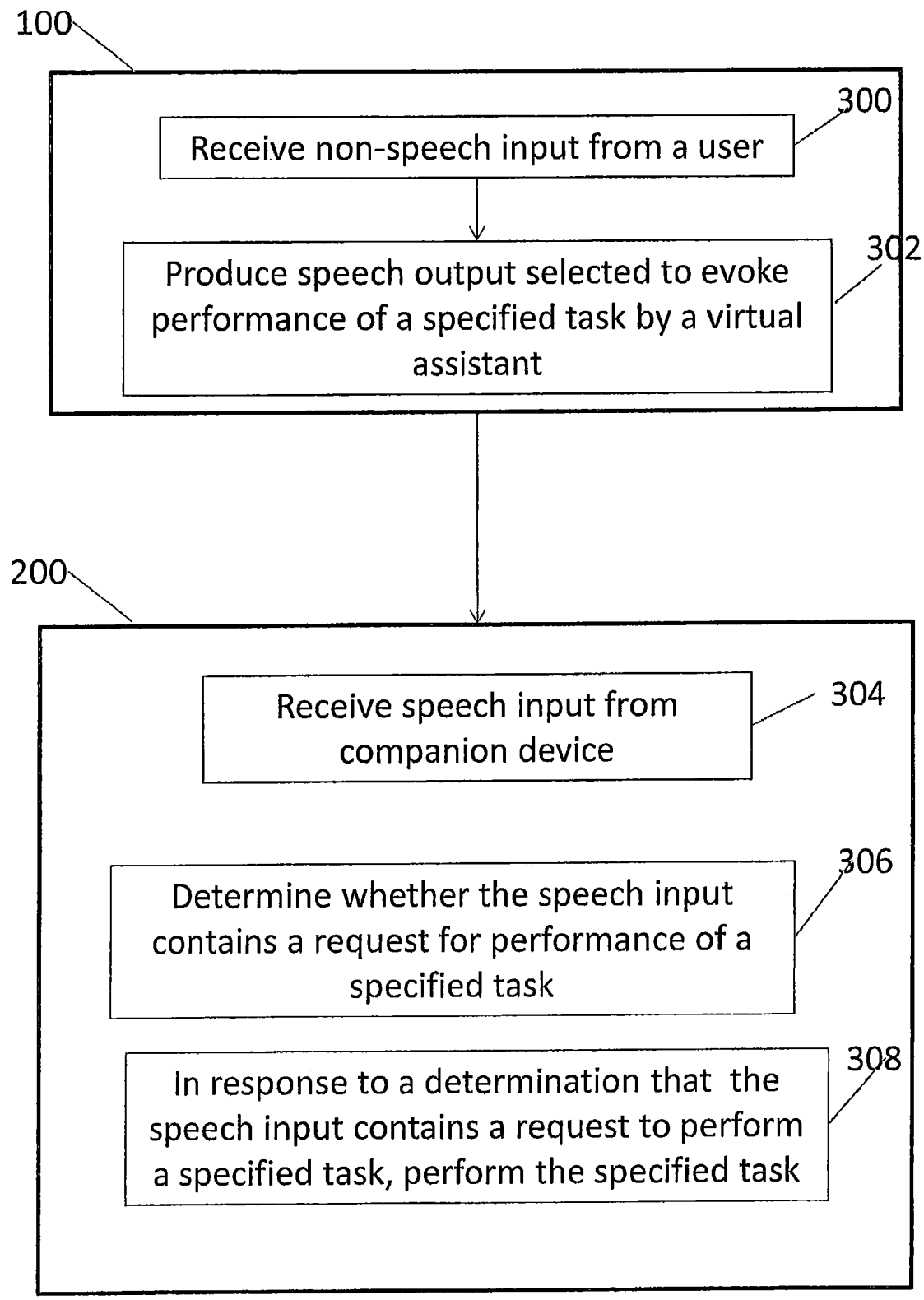

VIRTUAL ASSISTANT COMPANION DEVICES AND USES THEREOF

BACKGROUND

Virtual assistants provide a user interface that permits a user to interact with an electronic device such as a smartphone or other computing device using natural language in spoken and/or text form. A virtual assistant may analyze the input provided by the user and initiate the performance of one or more tasks based on the user's input. A wide range of tasks may be performed by an electronic device equipped with a virtual assistant, such as ordering products, playing music, or providing information such as weather or news. Some of the tasks may involve controlling other electronic devices that are equipped with appropriate software and connectivity. Some of the tasks may include "talking" to the user via a speaker.

A voice-based virtual assistant may perform speech recognition and natural language processing on spoken user input and attempt to infer what the user aims to achieve through his or her interaction with the virtual assistant. A voice-based virtual assistant may have sophisticated natural language understanding capabilities, thereby allowing considerable flexibility in how the user interacts with it. However, at present, many voice-based virtual assistants require use of specific commands in order to reliably invoke performance of a desired task.

SUMMARY

In some aspects, described herein is a device that relieves a user of a voice-based virtual assistant of the need to remember specific commands required to cause the virtual assistant to perform a particular task. In some aspects, the device stores pre-recorded or dynamically generated voice commands intended to communicate with and activate a voice recognition computer interface to initiate a session or otherwise provide fixed voice commands that "awake" or initiate a computer interactive voice session or cause a device having a voice-based user interface to perform a specified task. In certain embodiments the device activates a virtual assistant and causes it to perform a specified task.

In some aspects, described herein is a method for operating a voice-based virtual assistant or device comprising a voice-based virtual assistant, the method comprising: receiving, at a first electronic device comprising or connected to a virtual assistant, an audio input comprising recorded or synthetic speech emanating from a second electronic device in response to a user input to said second electronic device; determining whether the audio input comprises a predetermined command; and, in accordance with a determination that input comprises a predetermined command, responding to the command. In some embodiments the user input comprises a manual input, such as pushing a button or flipping a switch. In some embodiments the second electronic device comprises a non-transitory storage medium having the command recorded thereon. In some embodiments the second electronic device comprises a digital voice recorder or voice synthesizer. In some embodiments the second electronic device further comprises any one or more of: (a) a programmable timer; (b) a light; (c) an alarm; (d) a motion detector; and (e) a proximity detector. In some embodiments the first electronic device comprises a smart speaker. In some embodiments the predetermined command causes the first electronic device to initiate an interactive voice session. In some embodiments the predetermined command causes the first electronic device to initiate an interactive health session. In some embodiments the predetermined command causes the first electronic device to tell the user to initiate an interactive health session. In some embodiments the predetermined command causes the first electronic device to tell the user to initiate an interactive health session with a second electronic device, optionally wherein the second electronic device is a mobile device. In some embodiments the first electronic device comprises a smart speaker or other device capable of producing sound, and conducting the interactive health evaluation comprises the smart speaker or other device requesting one or more items of health data from the user, e.g., by asking the user one or more health-related questions.

In some aspects, described herein is a method for facilitating operation of a voice-based virtual assistant or device comprising a voice-based virtual assistant by a user, said virtual assistant being associated with a first electronic device, the method comprising: providing to the virtual assistant the capacity to recognize and respond to a predetermined spoken command; and providing to a user of said virtual assistant a second electronic device that utters recorded or synthetic speech comprising said predetermined spoken command in response to a user input. In some embodiments the user input comprises a manual input, optionally wherein said manual input comprises pushing a button or flipping a switch. In some embodiments the second electronic device comprises a non-transitory storage medium having the command recorded thereon. In some embodiments the second electronic device comprises a digital voice recorder or voice synthesizer. In some embodiments the second electronic device comprises any one or more of: (a) a programmable timer; (b) a light; (c) an alarm; (d) a motion detector; and (e) a proximity detector. In some embodiments the response to the predetermined spoken command comprises initiating an interactive voice session. In some embodiments the response to the predetermined spoken command comprises initiating or instructing the user to initiate an interactive health session. In some embodiments the response to the predetermined spoken command comprises instructing the user to initiate an interactive health session with a second electronic device, optionally wherein the second electronic device is a mobile device. In some embodiments the first electronic device comprises a smart speaker or other device that is capable of producing sound, and conducting the interactive health evaluation comprises the smart speaker or other device requesting one or more items of health data from the user, e.g., by asking the user one or more health-related questions.

In some aspects, described herein is a non-transitory computer-readable medium comprising instructions for: receiving, at a first electronic device, an audio input comprising recorded or synthetic speech emanating from a second electronic device in response to a user input; determining whether the audio input comprises a predetermined command that corresponds to a specific task; and, in accordance with a determination that the input comprises a predetermined command, responding to the command by performing the task. In some embodiments the first electronic device is a smart speaker. In some embodiments the task comprises initiating or instructing a user to initiate an interactive health session.

In some aspects, described herein is a system comprising: one or more processors; memory storing one or more programs configured to be executed by the one or more processors, the one or more programs including instructions for: receiving, at a first electronic device, an audio input comprising recorded or synthetic speech emanating from a second electronic device in response to a user input to said second electronic device; determining whether the input comprises a predetermined command that corresponds to a specific task; and, in accordance with a determination that the input comprises a predetermined command, responding to the command by performing the task. In some embodiments the first electronic device comprises a smart speaker. In some embodiments the task comprises initiating or instructing a user to initiate an interactive health session.

In some aspects, described herein is a system comprising: (a) a first electronic device comprising a voice-based virtual assistant; and (b) a virtual assistant companion device capable of speaking a command that activates a voice-based virtual assistant and/or causes it to perform a specified task. In some embodiments the virtual assistant companion device comprises a non-transitory storage medium having a command recorded thereon. In some embodiments the virtual assistant companion device comprises a digital voice recorder or voice synthesizer. In some embodiments the virtual assistant companion device further comprises any one or more of: (a) a programmable timer; (b) a light; (c) an alarm; (d) a motion detector; and (e) a proximity detector. In some embodiments the first electronic device comprises a smart speaker.

BRIEF DESCRIPTION OF THE DRAWING

FIG. 1 is a flow chart illustrating operation of a virtual assistant companion device in accordance with some embodiments.

DETAILED DESCRIPTION

The terms "virtual assistant", "intelligent automated assistant", and "intelligent personal assistant" refer to an information processing system that interprets natural language input in spoken and/or textual form to deduce user intent and performs actions based on the deduced user intent. Typically, the user seeks either an informational answer or performance of a task by the virtual assistant. A satisfactory response to the user request is typically provision of the requested informational answer, performance of the requested task, or a combination of the two. To act on a deduced user intent, the system may perform one or more of the following: identify a task flow with steps and parameters designed to accomplish the deduced user intent, input specific requirements from the deduced user intent into the task flow; execute the task flow by invoking programs (software applications), methods, services, APIs, or the like; and generate output responses to the user in an audible (e.g. speech) and/or visual form.

A virtual assistant that accepts spoken input may be referred to as a "voice-based virtual assistant". A voice-based virtual assistant is capable of accepting a user request at least partially in the form of a spoken natural language command, request, statement, narrative, and/or inquiry. The term "command" is used interchangeably with "request". A command may be any word or sequence of two or more words. One of ordinary skill in the art will appreciate that a command may be in the form of a statement, narrative, and/or inquiry. A voice-based virtual assistant may use any of a variety of speech recognition technologies (also referred to as voice recognition technologies) to recognize the spoken words.

The effectiveness of a virtual assistant depends to a significant extent on the assistant's ability to deduce the correct task(s) to perform from the user request expressed in natural language. A user may express a particular user intent in any of numerous ways that would be understood by a human being. A virtual assistant may sometimes have the ability to correctly infer a particular user intent based on any of a variety of speech inputs. However, speech recognition and natural language processing capabilities of virtual assistants can vary with regard to their ability to recognize and correctly act on a wide variety of speech inputs. It may sometimes be necessary to utter a specific, predetermined word or sequence of words or one of a limited number of predetermined words or sequences of words in order to evoke performance of a particular desired task. In some instances, utterances that would be understood by a human as embodying the same request may not be understood as equivalent by a virtual assistant, resulting in failure to execute the appropriate task. For example, the request "Ask Plume for air pollution level in Los Angeles" may produce an appropriate result while the phrase "What is the air pollution level in Los Angeles?" may produce a result of "I cannot find an answer to the question I heard".

In some instances, a virtual assistant is only capable of selecting the appropriate program or service with which to perform a task if a specific word or phrase corresponding to that program or service is included in the command. In some instances, a virtual assistant may not be capable of reliably recognizing words spoken with an accent. In some instances, the ability of a virtual assistant to recognize words may be limited to one or a small number of languages. Such limitations may hinder the effective use of virtual assistants.

In some aspects, described herein is a device that relieves a user of a voice-based virtual assistant of the need to remember and speak specific commands that activate the virtual assistant to perform a particular task. The device, which may be referred to herein as a "virtual assistant companion", "virtual assistant companion device", or "companion device", stores one or more pre-recorded voice commands or dynamically generates one or more specified voice commands, wherein the pre-recorded or dynamically generated voice command(s) are capable of activating a virtual assistant that has a voice-based user interface, and/or causing the virtual assistant to perform a specific task. Upon activation by a user, typically via a non-speech input, the virtual assistant companion speaks the voice command, thereby causing the virtual assistant to perform the task.

An electronic device that is equipped with a voice-based virtual assistant may be referred to as a "primary device". A primary device may be any electronic device that comprises or interfaces with one or more microphones for converting sound waves (e.g., from speech) into electrical signals. A primary device may comprise or interface with one or more speakers that convert electrical signals into sound. In some embodiments a primary device is a mobile device such as a smartphone. In some embodiments a primary device comprises a smart speaker. In some embodiments a primary device is a laptop or desktop computer, a television, a remote control, or a game console. Through interacting with other electronic devices or networks, a primary device may offer a wide variety of applications, such as Voice over Internet Protocol (VOIP) telephony, audio streaming, making to-do lists, setting alarms, providing weather and other real time information, ordering products, and home automation. A virtual assistant may select the appropriate applications to fulfill a user's wishes based on user input.

Virtual Assistants

In general, a virtual assistant companion may be used to issue commands to any voice-based virtual assistant. One of ordinary skill in the art will appreciate that a virtual assistant may be implemented in a variety of ways. Non-limiting examples of virtual assistants and their implementation may be found in, e.g., U.S. Patent Application Publication Nos. 20120016678, 20140370841, 20150186156, and 20160093304, the disclosures of each of which are hereby incorporated by reference in their entireties. For example, a virtual assistant may be implemented according to a client-server model wherein the virtual assistant includes a client-side portion that executes on a user device and a server-side portion that executes on a server system. The virtual assistant client communicates with the server through one or more networks. The client provides client-side functionalities such as user-facing input and output processing and communications with the server. The server typically provides server-side functionalities for any number of clients, each residing on a respective user device.

In some embodiments, the server includes a client-facing I/O interface, one or more processing modules, data and models, and an I/O interface to external services. The client-facing I/O interface facilitates the client-facing input and output processing for the digital assistant server. The one or more processing modules utilize the data and models to determine the user's intent based on natural language input and perform task execution based on deduced user intent. In some embodiments, the server communicates with external services through the network(s) for task completion or information acquisition. The I/O interface to external services facilitates such communications.

Examples of the communication network(s) include local area networks ("LAN") and wide area networks ("WAN"), e.g., the Internet. The communication network(s) may be implemented using any known network standard or protocol, including various wired or wireless standards and protocols, such as e.g., Ethernet, Universal Serial Bus (USB), FIREWIRE, Global System for Mobile Communications (GSM), Enhanced Data GSM Environment (EDGE), code division multiple access (CDMA), time division multiple access (TDMA), Bluetooth, Wi-Fi, Internet Protocol (IP), voice over Internet Protocol (VoIP), Wi-MAX, or any other suitable communication standard or protocol.

The server system may be implemented on one or more standalone data processing apparatus or a distributed network of computers. In some embodiments, the server system may also employ various virtual devices and/or services of third party service providers (e.g., third-party cloud service providers) to provide the underlying computing resources and/or infrastructure resources of the server system. The division of functionalities between the client and server portions of the virtual assistant can vary in different embodiments. For example, in some embodiments, the client provides only user-facing input and output processing functions and delegates all other functionalities of the virtual assistant to a backend server. For example, audio input collected by the primary device's microphone(s) may be streamed to the cloud and processed remotely by the virtual assistant software. The remote server may communicate with the primary device to control its output.

In some embodiments, the functions of a virtual assistant are implemented as a standalone application installed on a user device.

In some embodiments, a virtual assistant includes a main natural language processing module that is used by the virtual assistant during normal operation and a limited natural language processing module that recognizes one or more of the predetermined speech inputs that a virtual assistant companion can speak. In some embodiments the limited natural language processing module is implemented on the primary device and the main natural language processing module is implemented on a remote server. The primary device may utilize the limited natural language processing module if the main language processor is not accessible, e.g., if connectivity to the remote server is lost.

A number of commercially available electronic devices are equipped with voice-based virtual assistants. For example, "Alexa" (Amazon, Inc.) is a voice-based virtual assistant that interacts with users via smart speakers known as Amazon Echo and Echo Dot. "Google Assistant" is a voice-based virtual assistant that is available with a smart speaker known as Google Home and smartphones known as Pixel. Siri (Apple, Inc.) is a voice-based virtual assistant that is part of Apple Inc.'s iOS, watchOS, macOS, and tvOS operating systems and is available on iPhones, iPads, and a variety of other electronic devices. Cortana (Microsoft, Inc.) is a voice-based virtual assistant that is available on computers running Windows 10 and smartphones running Windows 10 Mobile, among others. Viv (Samsung) a voice-based virtual assistant that may in the future be available on Samsung smartphones. For purposes of description herein, it is sometimes assumed that a virtual assistant companion is used with the virtual assistant Alexa and that the primary device comprises a smart speaker. However, it should be understood that a virtual assistant companion may be used with any voice-based virtual assistant and any type of primary device.

Virtual Assistant Companion

FIG. 1 is a flow chart illustrating operation of a virtual assistant companion device in accordance with some embodiments. In accordance with these embodiments, a virtual assistant companion device (100) receives (300) a non-speech input from a user and produces speech output (302), which serves as audio input (304) to a primary device (200). In some embodiments or circumstances, the primary device determines (306) whether the speech input expresses a user request for performing a specific task. In some embodiments, in response to determining that the speech input expresses a request for performing a specific task (308), the virtual assistant performs the task. It should be understood that wherever a primary device or virtual assistant is referred to as determining something, the determination may be performed by the primary device (e.g., by a executing one or more computer-readable instructions on a processor that is part of the primary device), may be obtained from a different device (e.g., from a remote server), or a combination thereof.

As described above, in some embodiments of the disclosed technology, upon activation by a user, a virtual assistant companion produces a spoken command that causes a virtual assistant to perform a specific task or tasks. The command serves as audio input to the primary device. A virtual assistant companion may be implemented in any of a variety of ways. In some embodiments a virtual assistant companion device stores a recorded command that is played when the device is activated. The virtual assistant companion device may comprise a non-transitory medium having one or more recorded commands stored thereon. The medium may be any medium on which sound can be recorded, e.g., a semiconductor, magnetic, or optical storage medium. The recording may be analog or digital. The command may be stored as one or more digital audio files encoding the command stored on a non-transitory computer-readable medium. The audio file may be in any format. The virtual assistant companion may further comprise one or more processors, transducers, or converters (which may comprise hardware, software, or a combination thereof), for converting the stored data into an electrical signal.

In some embodiments, the virtual assistant companion comprises a recording device that plays back a recorded command when the virtual assistant companion is activated. The recording device is typically a digital voice recorder but may alternatively be an analog voice recorder. In some embodiments the virtual assistant companion may be supplied to the user with a command already recorded on a recording device. In some embodiments the user may, if desired, record a different command that replaces the original command or record one or more additional commands.

In some embodiments the virtual assistant companion comprises a voice synthesizer that generates the command dynamically upon user input. The voice synthesizer may be programmed to utter the command.

In some embodiments, upon activation, the virtual assistant companion may access a remotely stored audio data file that encodes the command. In some embodiments, upon activation, the virtual assistant companion may access a remotely located voice synthesizer that generates the command. In some embodiments the virtual assistant companion may access the remotely stored file or voice synthesizer over a network e.g., the Internet. The virtual assistant companion may download the data file or output of the voice synthesizer or obtain it by streaming. In some embodiments the virtual assistant companion may store a downloaded file and use it subsequently upon activation of the device or may access the remotely stored file or remotely located voice synthesizer each time upon activation.

In general, a virtual assistant companion comprises a component that is capable of producing sound. For example, a virtual assistant companion typically comprises one or more speakers that emit the command upon activation of the device and may comprise one or more amplifiers for amplifying the signal that drives the speaker.

The components of the companion device may be housed in a suitable housing. The housing may, for example, be made of plastic, metal, ceramic, or other suitable material(s) or combinations thereof. One of ordinary skill in the art will appreciate that a virtual assistant companion may have any of a wide variety of shapes and dimensions. In some embodiments the device may be cuboidal or cylindrical. In some embodiments the virtual assistant companion may weigh between 1 and 8 ounces. In some embodiments the largest dimension of the virtual assistant companion is between 2 inches and 6 inches.

The virtual assistant companion is typically activated using non-speech input, e.g., manually. To that end, a virtual assistant companion may comprise a switch or other control means that, when activated (e.g., manually), causes the recording device to play the command or the synthesizer to generate the command. The switch may be, e.g., a push button switch or a toggle switch or a touch switch. One or more switches or other control means for use to activate the virtual assistant companion may be mounted on or in the housing such that they are accessible to the user. In some embodiments, a switch or housing may bear a word or image that is indicative of the particular command that will be spoken when the virtual assistant companion is activated or the task that will be performed by the virtual assistant in response to the command uttered by the virtual assistant companion. For example, if the command is one that would cause the virtual assistant to order a pizza, the image may be a picture of a pizza. In some embodiments the virtual assistant companion is capable of speaking two or more different commands. In such embodiments, the virtual assistant companion may comprise two or more switches (or other control means). Each such switch (or other control means) may be labeled with a word or image indicative of the particular command that will be spoken when that switch (or other control means) is activated. In some embodiments a virtual assistant companion comprises a touch screen. The touch screen may comprise an icon that, when touched, causes activation of the virtual assistant companion. In some embodiments the touch screen comprises two or more icons each of which may comprise a word or image indicative of a particular command that will be spoken when that icon is touched.

In some embodiments the volume at which the virtual assistant companion speaks a command may be controllable by the user. To that end, the virtual assistant companion may comprise a volume control, which may include a knob or slider that can be used to adjust the volume.

In some embodiments the virtual assistant companion housing has a flat base so that it can be easily positioned on a flat surface such as a table or counter top. In some embodiments the housing comprises a magnet, suction cup, adhesive sticker, or other mounting means that can be used to affix the device to a surface. The magnet, suction cup, adhesive sticker, or other mounting means may be placed on one side of the housing, with the activating means being located on the opposite side. In some embodiments a virtual assistant companion may be attachable to a lanyard so that the user can "wear" the device around his or her neck, shoulder, arm, or wrist. To that end, the housing may have a small hole in a corner or edge or a tab with a hole in it may project from the housing. Such a hole could alternatively or additionally be used to thread a cord that could be used to hang the virtual assistant companion from a peg or hook or other attachment means or otherwise attach or tether the virtual assistant companion to a wall, appliance furniture, or the like.

In some embodiments the companion device may have a programmable timer that can initiate the voice command at any scheduled time. For example, the timer may be set such that the companion device issues a voice command that causes the virtual assistant to perform an interactive health evaluation (discussed further below) each day at the same time.

In some embodiments the companion device may have a light that turns on, changes color, or flashes as a visual prompt for the user to activate the companion device. The time at which the light and/or alarm prompts the user may be programmable. The time may have a default value that would be used if no value is selected. In some embodiments the light or alarm can be restored to its usual state (e.g., turned off) by the user, e.g., using a switch. In some embodiments the act of restoring the light or alarm to its usual state activates the companion device.

In some embodiments the companion device may have a motion detector, occupancy detector, and/or proximity detector. In some embodiments the companion device may be configured such that the alarm or flashing light turns on only if the companion device has sensed movement or the presence of a person within a certain distance and/or over a certain period of time. If the companion device has not sensed movement or the presence of a person within a certain distance and/or over a certain period of time, the alarm or flashing light may delay turning on until such movement or presence is sensed. The distance and/or time may be programmable. The distance and/or time may have default values that would be used if no value is selected. In some embodiments the companion device may be configured such that the alarm or flashing light only turns on when the companion device has sensed that an individual is in the same room as the device. In some embodiments a proximity detector comprises a sensor that senses an RF ID tag. In some embodiments a watchband or other wearable device or clothing could include such a tag. In some embodiments, proximity of the tag to the companion triggers an utterance.

In some embodiments the companion device is battery operated. The batter(ies) may be non-rechargeable or rechargeable.

In general, a companion device may be positioned anywhere sufficiently close to a primary device such that audio output emitted from the companion device will be detected and can be correctly interpreted. The appropriate distance will typically depend on the volume of the speech emitted by the companion device and the distance between the companion device and the primary device. In some embodiments the companion device may be positioned less than 6 feet from the device or within 6-10 feet from the device. In some embodiments the companion device may be located more distantly from the primary device. In some embodiments a companion device may be located within the same room as the primary device. The companion device is typically portable and can be placed at any convenient location.

In some embodiments, when appropriately positioned with respect to the primary device, activation of the virtual assistant companion results in performance of the task corresponding to a particular command with a high degree of reliability. For example, in some embodiments, assuming that the primary device is functioning properly, the task is performed with a likelihood of at least 95%, 96%, 97%, 98%, 99%, 99.5%, 99.6%, 99.7%, 99.8%, 99.9%, or more following activation of the companion device.

Commands and Tasks

In general, a command may comprise any one or more words. A command may begin with a "wake word", which term refers to a word or phrase that activates a primary device, causing the word(s) following the wake word to be considered as a potential command. For example, the words "Alexa", "Amazon", and "echo" serve as wake words for Amazon's Echo and Dot devices. Upon recognition of the wake word at a primary device, the virtual assistant attempts to recognize subsequent words and deduce the user's intent and then performs the appropriate task(s). In some embodiments, upon recognition of a wake word, subsequent words are streamed to the cloud and analyzed remotely by the virtual assistant.

A command may contain any one or more words that can be recognized by the virtual assistant. A command is usually a sequence of words that would be understood by a typical user as conveying a particular intent. A command usually contains at least one verb and at least one noun, and may contain one or more additional types of words such as prepositions, conjunctions, adverbs, adjectives, etc. However, the invention is not limited with respect to the nature of the commands.

In some embodiments, a command may contain one or more words that identifies a specific software application or service that the virtual assistant is capable of invoking and serves to indicate that that particular software application or service is to be utilized to carry out the task. The one or more words may be referred to as a "trigger phrase", which may use various structures to define the command. For example, the structure "w, ask x to do y" could be used, in which w refers to the wake word, x refers to an application which is to be utilized to perform a task, and y refer to the task to be performed. Thus, using this structure, in some embodiments, a virtual assistant companion could generate the command, "Alexa, ask Garageio to open the garage.", which would in turn cause Alexa to invoke the smart home garage door controller known as Garageio (Alottazs Labs LLC) in order to open the user's garage door. Another example is the command "Alexa, ask Lyft for a ride.", which would invoke a software application of the transportation network company Lyft to request a ride for the user. Other structures are also possible. For example, the structure "w, start x" or "w, open x" could be used to simply request that the virtual assistant open a particular software application or service named in the command. In some embodiments, if a command does not include one or more words that serve to indicate that that particular software application or service is to be invoked, the virtual assistant may ascertain the appropriate software application or service to invoke based on the content of the command.

A virtual assistant may perform any of a wide variety of tasks in response to a command. The invention is not limited with respect to the nature of the tasks that may be carried out by a virtual assistant in response to a command spoken by a virtual assistant companion. In some embodiments a task comprises conducting an interactive voice session with the user. "Interactive voice session" refers to a series of interactions between a user and a system comprising a virtual assistant that takes place using spoken language. The virtual assistant companion relieves the user of the need to recall and speak specific words that activate an interaction with the virtual assistant. An interactive voice session may include one or more requests for information directed to the user by the virtual assistant. In some embodiments the information requested relates to the command that initiated the interactive voice session and permits the virtual assistant to more specifically deduce the user's intent. For example, if the command is "Alexa, help me order food.", an interactive voice session might include questions asking the user about what type and quantity of food he or she wishes to order, asking the user about restaurant preferences, etc. The virtual assistant may engage the user in a dialog until the virtual assistant has obtained sufficient information to carry out the task of placing a specific order with a particular restaurant based on the user's input.

Interactive Health Data Collection and Evaluation

In some aspects, a virtual assistant, e.g., a virtual assistant with a voice-based user interface interfaces with or serves as part of a system for health tracking and management. In some embodiments a virtual assistant executes a task that comprises collecting health data from a user. In some embodiments, health data are collected at least in part by performing an interactive health session. The term "interactive health session" refers to an interaction between a user and a system in which the system presents one or more requests for health data and the user provides responses. The health data may pertain to symptoms, physiological variables, or other variables that are of use in monitoring or evaluating the user's health status and/or assessing the safety, tolerability, or efficacy of a therapeutic agent, medical device, or treatment approach (outcomes data). A request may, for example, ask the user about the presence, quality, or severity of a symptom or ask the user to provide physiological data (e.g., a value of a physiological variable such as blood pressure, heart rate, oxygen saturation, etc.) obtained using a monitoring device. In some embodiments an interactive health session requests numerical values or responses to questions asked in a yes/no or multiple choice format. In some embodiments, the virtual assistant may provide spoken instructions to the user regarding how to gather or input the data requested in an interactive health session. For example, the virtual assistant may tell the user which monitoring devices to use and/or how to use them.

The user may provide the requested health data in a variety of ways, e.g., as text or voice input, depending on the user interface of the device that interacts with the user to conduct the health session. In some embodiments an interactive health session may ask the user to measure a physiological variable using a connected monitoring device. The relevant value is transmitted from the connected monitoring device to the system or to a location from which it will be accessible to the system, thus relieving the user of the need to input the data.

In some embodiments, a system that conducts an interactive health session stores the health data on a computer-readable medium in association with a user identifier. The data may be used by the user or a health care provider of the user in order to track or manage the user's health. In some embodiments an interactive health session may be performed on a regular schedule, e.g., daily.

In some embodiments, a system that conducts an interactive health session may evaluate one or more items of health data received from the user. Such an evaluation may include any type of analysis, examination, or interpretation of the data. For example, the system may determine whether the data is within the normal range, whether the data indicates a deterioration or improvement in the user's condition, etc. An interactive health session in which at least some of the health data that is collected is also evaluated may be referred to as an "interactive health evaluation". Wherever the term "interactive health session" is used herein, the interactive health session may be an interactive health evaluation.

In some embodiments an interactive health evaluation collects one or more items of physiological data and evaluates the data to determine whether to collect additional data. In some embodiments an aberrant value of a physiological data element, which may be referred to as a "sign" may trigger one or more requests for additional health data. In some embodiments at least some of the additional health data requested pertains to symptoms that the user may have.

In some aspects, an interactive health evaluation relates at least in part, or primarily, to a particular condition. In some embodiments, an interactive health evaluation may be designed to detect clinically significant health changes with respect to a particular condition. In some embodiments, the health data obtained through an interactive health evaluation are processed and used, optionally together with other data, such as health data previously entered by the user, to assess the likelihood that the user is at risk of or is experiencing an exacerbation of the condition.

In some embodiments, the health data obtained through an interactive health evaluation are processed and used, optionally together with other data, such as health data previously entered by the user, to make recommendations or take actions. For example, the system may recommend that the user contact his or her health care provider to seek medical advice immediately, contact his or her health care provider to set up an outpatient appointment, seek care at an urgent care clinic or other health care facility, or seek emergency medical attention (such as by calling "911") or may indicate that the user does not seem to be in need of medical attention. Actions that a system might take may include sending a message (e.g., to a user's health care provider or caregiver), and/or adjusting a timing or frequency for collecting health data from the user. In some embodiments, a software application or service that may be used to perform an interactive health evaluation may comprise a module (which may be referred to as a "Smart Symptom Tracker", or "SST") that includes computer-executable instructions for collecting health data, analyzing that data, and making recommendations or taking actions based on the results of that analysis. In some embodiments the health data includes at least some symptom data. In some embodiments it is envisioned that a user would perform an interactive health evaluation during which one or more physiological variables would be measured and entered into the system. In some embodiments it is envisioned that such an interactive health evaluation would be performed on a regular basis, e.g., daily, so that the values of such variables would be tracked. In some embodiments, if an aberrant physiological data element is detected during such an interactive health evaluation, the system would automatically determine whether to ask additional questions (e.g., one or more questions regarding symptoms) and/or make one or more recommendations or take one or more actions. In other words, the session would begin with requests for updates to physiological variables and would only proceed to the additional functions of an SST of collecting and analyzing symptom data and making recommendations and/or taking actions upon detection of physiological data of concern. In some embodiments a user may initiate execution of an interactive health evaluation that includes the functions of collecting and analyzing symptom data and making recommendations and/or taking actions at any time.

In some embodiments a command spoken by a virtual assistant companion causes a virtual assistant to execute a task that comprises collecting health data from the user. For example, in some embodiments a command spoken by a virtual assistant companion may cause the virtual assistant to initiate performance of an interactive health evaluation. An example of a command that may cause a virtual assistant to conduct an interactive health evaluation is, "Alexa, run my health tracker."

In some embodiments a virtual assistant may invoke a particular software application or service in order to perform an interactive health evaluation. For purposes of description, such a software application or service may be referred to herein as "Revon". In some embodiments a command to a virtual assistant, e.g., a command spoken by a virtual assistant companion in response to user input as described herein, may contain one or more words that identifies a specific software application or service that is to be utilized to perform an interactive health evaluation. For example, a command intended to cause a virtual assistant to invoke a software application or service known as "Revon" in order to conduct an interactive health evaluation may be, "Alexa, ask Revon to run my health tracker." or "Alexa, start Revon."

In some embodiments, a virtual assistant that has a voice-based user interface tells a user to initiate performance of an interactive health evaluation on an electronic device other than the primary device equipped with the virtual assistant. For purposes of description, such an electronic device may be referred to as a "second device". For example, in some embodiments a virtual assistant associated with a smart speaker may tell the user to initiate performance of an interactive health session on the user's mobile phone. In some embodiments the user may enter health data into the second device using a physical keypad or a touch screen.

In some embodiments a command spoken by a virtual assistant companion may cause a virtual assistant to tell the user to initiate performance of an interactive health evaluation on a second device. An example of a command that may cause a virtual assistant to tell the user to initiate performance of an interactive health evaluation on a second device is, "Alexa, start health check process." An example of an instruction that a virtual assistant may speak to tell the user to initiate performance of an interactive health evaluation on a second device is, "It's time for your daily health check. Start Revon on your smartphone."

In some aspects, a voice-based virtual assistant may serve as a user interface for systems and methods for health tracking and management, including systems and methods for performing an interactive health evaluation, such as those described in PCT/US2015/034875 (WO2015191562), PCT/US2015/060737 (WO2016077792), and/or U.S. Ser. No. 15/202,223, the disclosures of each of which are hereby incorporated by reference in their entireties. In some aspects, it is expressly contemplated to use a virtual assistant companion and a virtual assistant in conjunction with technology described in any one or more of said disclosures. In some embodiments, performing an interactive health evaluation or reviewing data collected during one or more interactive health evaluations may assist a user in self-management of their condition. In some embodiments, having access to health data collected during one or more interactive health evaluations may help a health care provider of the user manage the user's health.

Without limiting the disclosed technology in any way, a virtual assistant companion may be particularly useful to users who find it challenging to remember commands and/or who have difficulty speaking or speak with an accent that causes the virtual assistant to at least sometimes fail to recognize the command even if the correct words are spoken or do not speak a language that the virtual assistant is capable of processing through its speech recognition function. In some embodiments the user may have a health condition that limits his or her ability to remember and/or speak.

In some embodiments the disclosed technology may be used in the conduct of a clinical trial in which a virtual assistant is used to collect or facilitate collection of health data by, e.g., performing an interactive health session in which data of interest in the context of the trial is collected. The data collected may include outcome data, e.g., data pertaining to an outcome of interest in the trial. Without wishing to be bound by any theory, use of a virtual assistant companion device may help ensure that participants in the trial have a uniform and consistent experience in terms of using the virtual assistant, thus reducing a potential source of variability in the trial.

While the disclosed technology has been discussed herein mainly in relation to companion devices for virtual assistants, the disclosure encompasses use of a companion device as described herein to communicate with, e.g., to issue a command to, any device or machine that has a voice-based user interface. Such devices may include, for example, home appliances (e.g., dishwasher, refrigerator, freezer, washing machine, clothes dryer, coffee maker, electric kettle, cooking appliances (e.g., a slow cooker, oven, stove)), environment control device (e.g., an air conditioner, furnace, heater, fan), hot water heater, garage door opener, vacuum cleaner, home entertainment devices (e.g., television, digital media player, radio, DVD or CD player), cameras, computers, etc. In certain embodiments a companion device may be used to issue a command to a vehicle (e.g., a car, bus, truck, motorcycle, train, watercraft, aircraft), robot, drone, or other machine. In some embodiments, the command causes the device or machine to perform a specified task or tasks. In some embodiments the command causes the device or machine to initiate an interactive voice session. Accordingly, wherever the present disclosure describes systems, computer-readable media, or methods that include or relate to a virtual assistant or device comprising a virtual assistant, the disclosure provides analogous systems, computer-readable media, and methods that include or relate to a voice recognition user interface or device having a voice recognition user interface.

Accordingly, in light of the potential for variations and modifications to the material described explicitly herein, the disclosure of this document should not be treated as implying limits on the protection provided by this document or any related document. Instead, the protection provided by a document which claims the benefit of or is otherwise related to this document should be understood as being defined by its claims, when the terms in those claims which are explicitly defined under the "Explicit Definitions" heading are given their explicit definitions, and when all other terms are given their broadest reasonable interpretation as shown by a general purpose dictionary. To the extent that the interpretation which would be given to the claims based on the above disclosure is in any way narrower than the interpretation which would be given based on the explicit definitions under the "Explicit Definitions" heading and the broadest reasonable interpretation as provided by a general purpose dictionary, the interpretation provided by the explicit definitions under the "Explicit Definitions" heading and broadest reasonable interpretation as provided by a general purpose dictionary shall control, and the inconsistent usage of terms in the specification shall have no effect, unless and to the extent that any particular claim or claims is amended to incorporate a narrower interpretation or limitation or a narrower interpretation or limitation is clearly and unambiguously adopted by the applicant during the course of prosecution of a particular claim or claims. It should also be understood that where the above disclosure refers to a species of a term that is defined generically in the Explicit Definitions or is otherwise encompassed by a definition in the Explicit Definitions, such reference in the above disclosure would support use of the full scope of the corresponding definition in the Explicit Definitions, including the species thereof. Thus, the use of a specific term in a particular context in the above disclosure would support use of the corresponding generic term as defined in the Explicit Definitions (as well as species thereof). By way of example, references to a "smartphone" in various contexts in the above disclosure would support use of the term "mobile computing device" and species thereof in such contexts.

Explicit Definitions

When used in the claims, "activity tracking device" refers to a type of "monitoring device" (defined infra) for monitoring and tracking fitness-related physiological parameters such as movement (e.g., distance walked or run, steps climbed), calories used, heart rate, sleep-related physiological parameters such as sleep duration, sleep depth, and any of a variety of others. An activity tracking device may use a three-dimensional accelerometer to sense user movement and measure steps taken, which it may use, sometimes together with user data, to calculate metrics such as distance walked, calories burned, floors climbed, and activity duration and intensity. Often an activity tracking device is a wearable electronic device that is or can be synchronized, in many cases wirelessly, to a computer or mobile device such as a smartphone. An activity tracking device may in some embodiments monitor activity in a room or within a home by means of heat-sensing (e.g., infrared), light-sensing, or other devices that detect movement or heat without necessarily being worn by or connected to the patient. Such devices may, for example, determine whether a patient has deviated from his or her normal level of activity within a home, failed to get out of bed, etc.

When used in the claims, "based on" should be understood to mean that something is determined at least in part by the thing that it is indicated as being "based on." When a claim is written to require something to be completely determined by a thing, it will be described as being "based exclusively on" the thing. Where the above disclosure refers to something being based on a thing or things, it should be understood that that "something" may, in certain embodiments, be based exclusively on that thing or things, or on any particular proper subset of such things.

When used in the claims, "behavioral data" should be understood to refer to any data pertaining to the way an individual acts, particularly those ways that may affect or reflect the individual's health, examples of "behavioral data" include, but are not limited to, data pertaining to: the individual's diet, physical activity, sleep, smoking, use of drugs with addictive potential, the way an individual interacts with a system implemented with the disclosed technology and components thereof (e.g., time spent accessing or otherwise engaging with educational materials), and/or compliance with a treatment plan.

When used in the claims, a "computer" should be understood to refer to a device or group of devices (e.g., a device comprising a processor and a memory) capable of storing and executing instructions for performing one or more logical and/or physical operations on data to produce a result. A "computer" may include, for example, a single-core or multi-core microcontroller or microcomputer, a desktop, laptop or tablet computer, a smartphone, a server, or groups of the foregoing devices (e.g., a cluster of servers which are used in combination to perform operations on data for purposes such as redundancy and availability).

When used in the claims, "computer readable medium" should be understood to refer to any object, substance, or combination of objects or substances, capable of storing data or instructions in a form in which they can be retrieved and/or processed by a device. A computer readable medium should not be considered limited to any particular type or organization, and should be understood to include distributed and decentralized systems however they are physically or logically disposed, as well as storage objects of systems which are located in a defined and/or circumscribed physical and/or logical space.

When used in the claims, "condition" should be understood to refer to a circumstance or set of circumstances which can be used to characterize the state of an individual's health. Thus, a "condition" would include a health problem or abnormality or any state of abnormal or normal health or function for which an individual seeks or obtains care from a health care provider (e.g., any disease, disorder, or other diagnostic entity known to medical practitioners of ordinary skill). A "condition" would also include the state of good health which an individual might wish to maintain, but for which he or she would not necessarily seek or obtain care from a health care provider.

When used in the claims, in the context of health data "condition-centric" should be understood to mean that the relationship of the health data to a condition is the guiding principle used to determine which health data to obtain, analyze, store, and/or present to a user, and/or to determine how the health data are presented to a user.

When used in the claims, "data element" should be understood to refer to an individual unit of data, which may be indivisible or may consist of one or more data items. A data element may, for example, be something as simple as an individual measurement of a physiological variable such as body weight, a level of an analyte in a body fluid, or a patient's response to a yes/no question about the presence or severity of a symptom, or may be more complex, such as a medical image (e.g., an X-ray image), a pathology report, or the like.

When used in the claims, a "data element type" should be understood as being synonymous with a "type of data element," and should be understood to refer to a particular kind or category of data element. A data element type may have a specific name, e.g., "body weight", "cough severity change", "6 minute walk distance", or "chest X-ray" and a definition.

When used in the claims, to "determine" something should be understood to mean to produce or generate, compute, establish, or specify that thing. For example, something may be "determined" by selecting it from a group of alternatives or options, by analyzing data (e.g., by applying an algorithm to the data) to generate a result.

When used in the claims, "environmental data" refers to data concerning a patient's indoor or outdoor environment. In this context, "indoor environment" refers to inside the patient's home and/or workplace or such other place as the patient spends a significant amount of time (e.g., at least 10 hours per week), while "outdoor environment" refers to the environment outside of buildings, and can be measured with data such as outdoor temperature, and levels of pollen or pollutants or others substances in the air.

When used in the claims, "geographic data" should be understood to refer to data about a geographic region, which may include data about environmental conditions in a region or people in the region. It should be understood that "geographic data" may overlap with "population-based data" (defined infra) and that both "geographic data" and "population-based data" may include epidemiologic data, such as data about the prevalence of particular infectious diseases in the geographic region where a patient lives.

When used in the claims, "health care institution" should be understood as being synonymous with "health care facility" and should be understood to refer to an institution that provides health care to multiple persons on a systematic basis, such as a hospital, health clinic, health center, surgery center, skilled nursing facility, or physicians' practice.

When used in the claims, "health data" should be understood to refer to any data or information about or relating to an individual or group of individuals that is descriptive of, informative about, affects, or potentially affects the health of the individual or group of individuals in more than merely a tangential or insignificant way. Health data can include, for example, physiological data, symptom data, results of medical tests (e.g., clinical chemistry or other types of laboratory tests, imaging, pathology tests, or any other type of test that might be performed on a patient by or at the direction of a health care provider), genotypic data, behavioral data, environmental data, demographic data, demographic data, geographic data, population-based data.

When used in the claims, a "mobile computing device" (sometimes referred to simply as a "mobile device" herein) should be understood to refer to a computer adapted to be moved by a user and to be operable during such movement, such as by including a local power supply (e.g., a battery). Examples of "mobile computing devices" include, but are not limited to portable digital assistants (PDAs), "smartphones" (defined infra), tablet computers, and laptop computers. Often, a "mobile computing device" will weigh under about 1-2 pounds, e.g., between about 2-3 ounces and about 1.5 pounds. For example, a "smartphone" or PDA may weigh between about 3 ounces and about 6 ounces and have height and width dimensions in the range of less than about 7×5 inches and depth less than about 0.5-1.0 inch, though smaller or larger weight and/or dimensioned devices may also fall within the scope of "mobile computing device."

When used in the claims, "monitoring device" should be understood to refer to a device that can be used for detecting or measuring one or more physiological variables, environmental variables, or behavioral variables relevant to a patient. It should be understood that a "personal monitoring device" (defined infra) is included within the definition of "monitoring device" unless otherwise indicated. Examples of "monitoring devices" include body weight scales, pulse oximeters, blood pressure monitors, thermometers, activity tracking devices, heart rate monitors, blood glucose measuring devices (glucometers), stethoscopes, medication dispensers that in some way monitor medication usage, and any other devices capable of obtaining physiological data, environmental data, or behavioral data relating to an individual, e.g., a patient, in his or her daily life. A monitoring device may be a wearable monitoring device, skin patch, implanted monitoring device, swallowed monitoring device, or indwelling monitoring device.

When used in the claims, an "outcome" should be understood to refer to health measurements or actions which may be, but are not necessarily, the ultimate results of a particular course of treatment or intervention or may serve as indicators of whether, or to what extent, a course of treatment or intervention is controlling or ameliorating a condition or symptom). Examples of outcomes include oxygen saturation for COPD, and hemoglobin AIC for diabetes mellitus. An outcome may be a result of a procedure or laboratory test or the fact that a procedure was performed on the patient (e.g., administration of a medication). In general, a given condition can have one or more outcomes associated with it. Some conditions may be associated with a single outcome, whereas other conditions may be associated with multiple outcomes. In general, a given outcome can be associated with one or more conditions. Some outcomes may be associated with a single condition, whereas other outcomes may be associated with multiple conditions.

When used in the claims, a "patient" should be understood to be an individual who seeks or receives health care from a health care provider. Any user of a virtual assistant or virtual assistant companion may be a patient.

When used in the claims, "personal monitoring device" should be understood to refer to a monitoring device that can be used by a patient in his or her daily life (i.e., while he or she is not under care in a health care facility).

When used in the claims, "physiological data" should be understood to refer to any qualitative or quantitative measurement of any indicator of a biological state, function, structure, process, response, or condition in a patient.

When used in the claims, "population-based data" should be understood to refer to data about groups of individuals, e.g., groups of patients having a particular condition or living in a particular geographic region. In this context, a geographic region may be a city, county, zip code area, state, or any other region as defined or used in an implementation of the disclosed technology. It should be understood that "population-based data" may overlap with "geographic data," and that both "population-based data" and "geographic data" may include epidemiologic data, such as data about the prevalence of particular conditions, e.g., infectious diseases, in the geographic region where a patient lives.

When used in the claims, a "set" should be understood to refer to a collection of zero or more things, which may be referred to as "elements" of the set. A "subset" of a set A is a set which does not include any elements that are not also in A. A subset of a set may include all the elements of the set.

When used in the claims, a "smartphone" should be understood as any mobile electronic device that combines the functions of a wireless phone and a computer within a single handheld unit and is capable of web browsing and running software applications. A "smartphone" can be understood in contrast with a "basic mobile phone" (i.e., a mobile phone that allows a user to make and receive calls but lacks the capability of executing software applications), or a "fixed phone" (i.e., a hard-wired or cordless phone that makes use of a fixed phone line).

When used in the claims, a "smart speaker" is a wireless speaker that combines the traditional function of a speaker (i.e., converting an electrical audio signal into sound) with computer-enabled functionality that includes the ability to connect to other electronic devices (e.g., other smart devices such as smartphones, smart appliances) or networks (e.g., the Internet) via one or more wireless protocols such as Bluetooth, Wi-Fi, 3G, etc.

When used in the claims, a "symptom" should be understood to include things like headache, impaired ability to walk, shortness of breath and other items related to subjective aspects of patient health about which data can be collected.

When used in the claims, the term "connected", in reference to an electronic device such as a monitoring device, speaker, home appliance, refers to a device that is or can be connected to a communication network or to a computer that is or can be connected to a communication network such that data collected by the device can be obtained without a user entering the data manually. A computer, e.g., a mobile device, equipped with or in communication with one or more appropriate sensors may serve as a connected monitoring device. Connected monitoring devices also include implanted, indwelling, or swallowed devices that are capable of wirelessly transmitting physiological data to a computer. Connected monitoring devices may be located in (as an integral part) or on of a mobile device or mobile device case. A connected monitoring device is typically a personal monitoring device.

When used in the claims, the term "activity tracking device" refers to a monitoring device for monitoring and tracking fitness-related physiological parameters such as movement (e.g., distance walked or run, steps climbed), calories used, heart rate, sleep-related physiological parameters such as sleep duration, sleep depth, and any of a variety of others. An activity tracking device may use a three-dimensional accelerometer to sense user movement and measure steps taken, which it may use, sometimes together with user data, to calculate metrics such as distance walked, calories burned, floors climbed, and activity duration and intensity. Often an activity tracking device is a wearable electronic device that is or can be synchronized, in many cases wirelessly, to a computer or mobile device such as a smartphone. An activity tracking device may in some embodiments monitor activity in a room or within a home by means of heat-sensing (e.g., infrared), light-sensing, or other devices that detect movement or heat without necessarily being worn by or connected to the patient. Such devices may, for example, determine whether a patient has deviated from his or her normal level of activity within a home, failed to get out of bed, etc. In some embodiments, it is envisioned that data concerning the indoor environment of a patient may be detected using a dedicated device or a mobile device equipped with an appropriate sensor, e.g., a connected device in the patient's home such as connected home automation devices (e.g., Nest programmable thermostat).

When used in the claims, the term "condition" refers to a circumstance or set of circumstances which can be used to characterize the state of an individual's health. Thus, a "condition" would include a health problem or abnormality or any state of abnormal or normal health or function for which an individual seeks or obtains care from a health care provider. A "condition" would also include the state of good health which an individual might wish to maintain, but for which he or she would not necessarily seek or obtain care from a health care provider. "Condition" encompasses diseases, disorders, illnesses, injuries, disabilities, syndromes, symptoms, and health-related complaints. "Disease" refers to a health problem or abnormality or state of abnormal health or function and is used interchangeably herein with "disorder" or "illness". A condition may be a complication of a disease or may be a particular symptom or group of symptoms.

I claim:

1. A method for operating a voice-based virtual assistant, the method comprising:
   (a) receiving, at a first electronic device comprising or connected to a virtual assistant, an audio input comprising recorded or synthetic speech emanating from a second electronic device in response to a user input to said second electronic device;
   (b) determining whether the audio input comprises a predetermined command; and,
   (c) in accordance with a determination that the audio input comprises a predetermined command, responding to the command;
   wherein:
   (i) the second electronic device comprises a user prompter comprising one or more of (a) a light and (b) an alarm;
   (ii) the second electronic device comprises a prompt trigger comprising one or more of: (a) a programmable timer; (b) a motion detector; and (c) a proximity detector; and
   (iii) the method comprises prompting, with the user prompter and based on the prompt trigger, a user to activate the second electronic device.

2. The method of claim 1, wherein said user input comprises a manual input, wherein said manual input comprises pushing a button or flipping a switch.

3. The method of claim 1, wherein the second electronic device comprises a digital voice recorder.

4. The method of claim 1, wherein:
   the second electronic device comprises a programmable timer.

5. The method of claim 1, wherein the first electronic device comprises a smart speaker.

6. The method of claim 1, wherein:
   (i) the predetermined command causes the first electronic device to initiate an interactive health session; and
   (ii) the interactive health session comprises making one or more requests of a user, wherein the one or more requests comprise at least one of:
      (a) asking the user about presence, quality or severity of a symptom; and
      (b) asking the user to provide physiological data obtained using a monitoring device and providing instructions for the user regarding how to gather the physiological data.

7. The method of claim 1, wherein the predetermined command causes the first electronic device to tell the user to initiate an interactive health session.

8. A method for facilitating operation of a voice-based virtual assistant by a user, said virtual assistant being associated with a first electronic device, the method comprising:
   (a) providing to the virtual assistant the capacity to recognize and respond to a predetermined spoken command; and
   (b) providing to a user of said virtual assistant a second electronic device that audibly utters recorded or synthetic speech comprising said predetermined spoken command in response to a user input;
   wherein:
   (i) the second electronic device comprises a user prompter comprising one or more of: (a) a light and (b) an alarm;
   (ii) the second electronic device comprises a prompt trigger comprising one or more of: (a) a programmable timer; (b) a motion detector; and (c) a proximity detector; and
   (iii) the method comprises prompting, with the user prompter and based on the prompt trigger, a user to activate the second electronic device.

9. The method of claim 8, wherein said user input comprises a manual input, wherein said manual input comprises pushing a button or flipping a switch.

10. The method of claim 8, wherein the second electronic device comprises a digital voice recorder.

11. The method of claim 8, wherein:
    the second electronic device comprises a programmable timer.

12. The method of claim 8, wherein:
    (i) the first electronic device makes a response to the predetermined spoken command which comprises initiating an interactive health session;
    (ii) the interactive health session is an interactive evaluation session which comprises:
       (a) collecting one or more items of physiological data;
       (b) based on the one or more items of physiological data, determining whether to collect additional data;
       (c) based on the collected data:
          (I) determining whether the user is experiencing an exacerbation of a condition; and
          (II) determining whether to adjust frequency of collecting data from the user.

13. The method of claim 12, wherein the response to the predetermined spoken command comprises instructing the user to initiate an interactive health session with a third electronic device, wherein the third electronic device is a mobile device.

14. The method of claim 12, wherein the first electronic device comprises a smart speaker, and wherein conducting the interactive health evaluation comprises the smart speaker making one or more requests of the user, wherein the one or more requests comprise:
    (i) asking the user about presence, quality or severity of a symptom; and
    (ii) asking the user to provide physiological data obtained using a monitoring device and providing instructions for the user regarding how to gather the physiological data.

15. A non-transitory computer-readable storage medium comprising instructions for:

(a) receiving, at a first electronic device, an audio input comprising recorded speech emanating from a second electronic device in response to a user input;

(b) determining whether the audio input comprises a predetermined command that corresponds to a specific task; and, (c) in accordance with a determination that the audio input comprises the predetermined command, responding to the command by performing the task.

16. The non-transitory computer-readable storage medium of claim 15, wherein the first electronic device is a smart speaker.

17. The non-transitory computer-readable storage medium of claim 15, wherein:

(i) the task comprises instructing a user to initiate an interactive health session; and (ii) the interactive health session is an interactive evaluation session which comprises:

(a) collecting one or more items of physiological data;

(b) based on the one or more items of physiological data, determining whether to collect additional data;

(c) based on the collected data:

(I) determining whether the user is experiencing an exacerbation of a condition; and (II) determining whether to adjust timing of collecting data from the user.

18. A system comprising:

(a) one or more processors;

(b) memory storing one or more programs configured to be executed by the one or more processors, the one or more programs including instructions for:

(i) receiving, at a first electronic device, an audio input comprising recorded or synthetic speech emanating from a second electronic device in response to a user input to said second electronic device;

(ii) determining whether the audio input comprises a predetermined command that corresponds to a specific task; and, (iii) in accordance with a determination that the audio input comprises the predetermined command, responding to the command by performing the tasks;

wherein:

(i) the second electronic device comprises a user prompter comprising one or more of (a) a light and (b) an alarm;

(ii) the second electronic device comprises a prompt trigger comprising one or more of: (a) a programmable timer; (b) a motion detector; and (c) a proximity detector; and (iii) the second electronic device is configured to prompt, with the user prompter and based on the prompt trigger, a user to activate the second electronic device.

19. The system of claim 18, wherein the first electronic device comprises a smart speaker.

20. The system of claim 18, wherein:

(i) the task comprises initiating an interactive health session; and (ii) the interactive health session is an interactive evaluation session which comprises:

(a) collecting one or more items of physiological data;

(b) based on the one or more items of physiological data, determining whether to collect additional data;

(c) based on the collected data:

(I) determining whether a user is experiencing an exacerbation of a condition; and (II) determining whether to adjust frequency of collecting data from the user.

21. A system comprising:

(a) a first electronic device comprising a voice-based virtual assistant; and (b) a virtual assistant companion device configured to audibly communicate a predetermined spoken command to the first electronic device in response to a user input;

wherein:

(i) the virtual assistant companion device comprises a user prompter comprising one or more of (a) a light and (b) an alarm;

(ii) the virtual assistant companion device comprises a prompt trigger comprising one or more of: (a) a programmable timer; (b) a motion detector; and (c) a proximity detector; and (iii) the virtual assistant companion is configured to prompt, with the user prompter and based on the prompt trigger, a user to activate the virtual assistant companion.

22. The system of claim 21, wherein the virtual assistant companion device comprises a digital voice recorder.

23. The system of claim 21, wherein:

the virtual assistant companion device comprises a programmable timer.

24. The system of claim 21, wherein the first electronic device comprises a smart speaker.

* * * * *